(12) United States Patent
Welles et al.

(10) Patent No.: US 7,461,896 B2
(45) Date of Patent: Dec. 9, 2008

(54) SYSTEM AND DEVICE FOR MONITORING AND ASSISTING HUMAN GROSS MOTOR SKILLS

(75) Inventors: Devon M. Welles, Hillsboro, OR (US); Brooke E. Foucault, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 11/478,526

(22) Filed: Jun. 30, 2006

(65) Prior Publication Data

US 2008/0007103 A1   Jan. 10, 2008

(51) Int. Cl.
*A61G 5/14* (2006.01)
*A47C 1/02* (2006.01)
(52) U.S. Cl. .............. 297/330; 297/217.3; 297/DIG. 10
(58) Field of Classification Search ................ 297/330, 297/DIG. 10, 217.3
See application file for complete search history.

(56) References Cited

U.S. PATENT DOCUMENTS

| 5,931,532 | A  | * | 8/1999  | Kemmerer et al. ........... 297/330 |
| 6,033,021 | A  | * | 3/2000  | Udo et al. ................ 297/330 X |
| 7,246,856 | B2 | * | 7/2007  | Kruse et al. .................. 297/330 |
| 7,255,397 | B2 | * | 8/2007  | Olcheski ..................... 297/330 |
| 2004/0195876 | A1 | * | 10/2004 | Huiban .................... 297/217.3 |
| 2007/0108809 | A1 | * | 5/2007  | Kurrasch et al. ......... 297/217.3 |

* cited by examiner

*Primary Examiner*—Rodney B. White
(74) *Attorney, Agent, or Firm*—Darby & Darby PC

(57) ABSTRACT

A system includes a lift chair having sensors embedded therein to determine various factors such as the amount of pressure exerted in various portions of the chair, the activity level of the chair user, whether the chair is occupied and which user is currently occupying the chair, and how much assistance the chair provides the user. The information detected by the sensors can be transmitted via the Internet, for example, to a third party device, such as a doctor's personal computer, which is also hooked up to the internet and is capable of receiving periodic updates to monitor use of the chair or modify the rules that govern the use of the chair. The user can override the pre-set rules for use of the chair by using an override button on a user control device.

31 Claims, 4 Drawing Sheets

SYSTEM AND DEVICE FOR MONITORING AND ASSISTING HUMAN GROSS MOTOR SKILLS

FIELD OF INVENTION

The embodiments of the invention relate to a system and device for monitoring assisting human gross motor skills. More particularly, the embodiments of the invention relate to a lift chair with sensors which can communicate information to allow monitoring of the use of the lift chair.

BACKGROUND

Power operated lift recliner chairs are commonly used by persons needing assistance in transferring from a seated position to a standing position. Such chairs include a power operated lift mechanism which raises the chair and tilts it forwardly to bring its occupant to a standing position and in reverse lowers the occupant from a standing to a seated position. These chairs are expensive and are commonly made affordable through insurance, requiring a doctor's prescription. However, doctors are hesitant to prescribe lift chairs because they fear that the patient will rely too heavily on the chair to stand, leading to accelerated atrophy of major muscle groups.

DETAILED DESCRIPTION

According to an embodiment of the invention, a system includes a lift chair, a plurality of sensors embedded in the lift chair, a third party device and a communication device for communicating information from the plurality of sensors to the third party device. According to an embodiment of the invention, the communication device is a two-way communication device. The system may further include a user control device for controlling operation of the lift chair. Further, the controller may control operation of the lift chair based on a set of assistance rules stored therein. The user control device may include an override button to override the stored assistance rules to control operation of the chair. Further, the third party device may transmit assistance rules to the controller via the communication device. The plurality of sensors may include, but are not limited to, activity and presence sensors, pressure sensors and angle sensors. A notification device may be attached to the chair to receive information from the controller regarding operation of the chair and relaying the information to a user of the chair. The plurality of sensors may detect information including at least one of a user's interaction with the chair, how much force the user sits down with, how much the user pushed off arm rests of the chair, how long the user remains seated in the chair, how far the chair is reclined, how far the chair is raised and lowered, and an angle of a foot rest of the chair. According to a further embodiment, the third party may transmit a new set of assistance rules based on the information detected by the sensors.

According to yet a further embodiment the controller determines which of a plurality of previously registered users is occupying the chair based on information detected from the sensors, and controls operation of the chair based on a predetermined set of assistance rules stored for each respective user.

Figure 1:
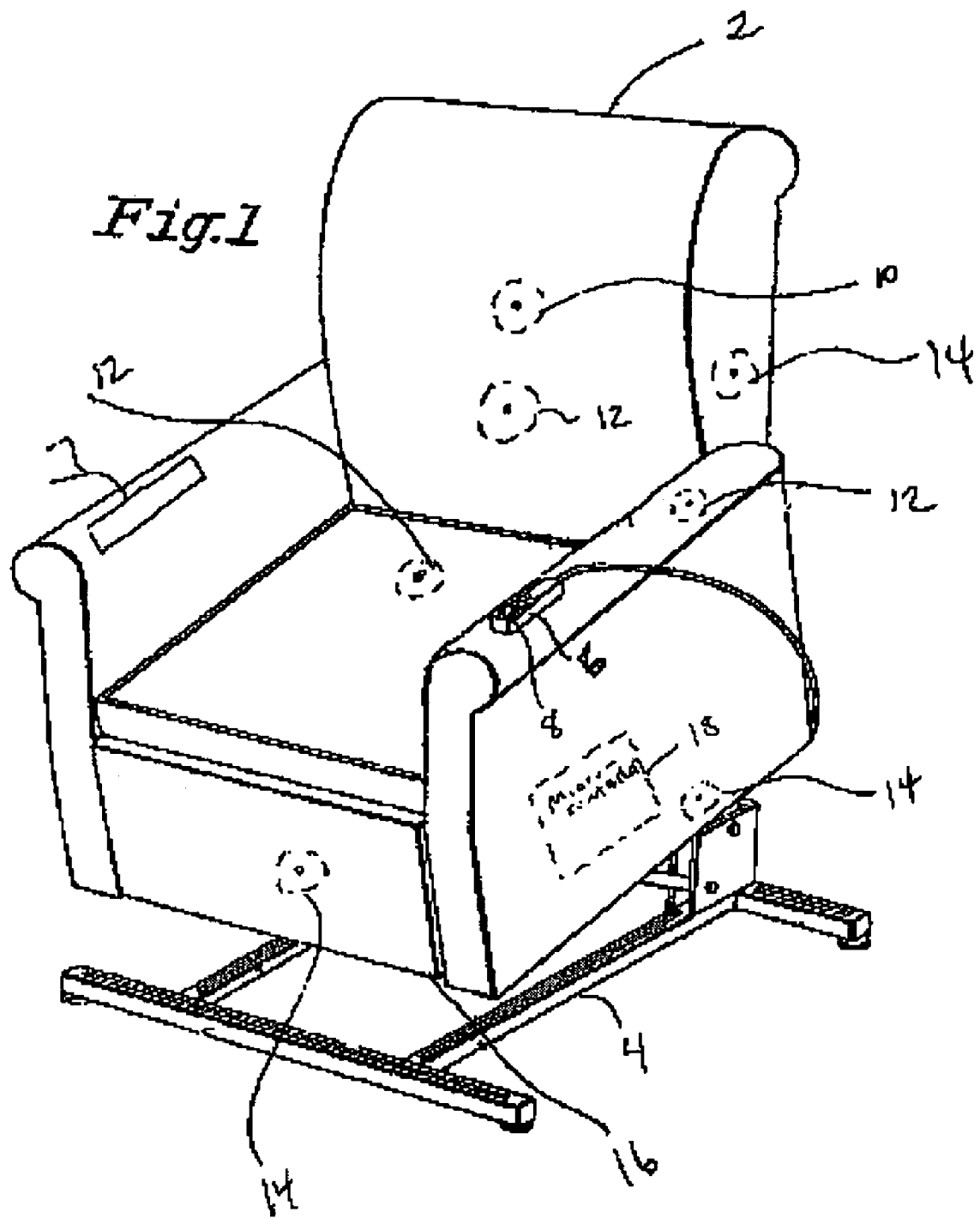
FIG. 1 shows a front perspective view of the lift recliner incorporating the sensor system of an embodiment of the invention.

FIG. 1 shows an automatic lift chair according to an embodiment of the invention. The lift chair and its operation described below is conventional and those in the industry are very familiar with the detailed construction and operation of such chairs. According to the invention, an automatic lift chair according to an embodiment of the invention comprises a microprocessor, an internal clock like that in all modern PCs, a communication device, a storage device such as a hard drive, flash memory, etc for storing assistance rules and data from the sensors, an override input, a feedback device, such as a screen, audible alerts, or any other way known to notify the user, and a plurality of sensors to detect the position of the chair, to detect if the user is sleeping, awake, etc., as will be explained herein in detail.

Referring to the drawings, FIG. 1 shows an automatic lift chair 2 which rests on a base 4 and includes a mechanism, such as a lift motor (not illustrated) for raising and lowering the chair. A user of the chair can control the various functions of the chair, such as raising the leg rest, changing the angle of the back, raising and lowering the chair, etc., through a user control device 6, which may include an override button 8 which allows the user to override previously programmed protocol for use of the chair in an emergency, for example.

The chair 2 may include multiple sensors, including but not limited to, activity and presence sensor 10 and pressure sensors 12 located in, for example, the back of the chair, the seat of the chair and each arm rest. The chair may also include various angle sensors 14 to determine the angle of the chair itself (i.e., how high the chair is raised), the angle of the leg rest 16, the angle of the back of the chair, and other such angles which are indicative of how the chair is being utilized.

The chair could also include a notification device, such as a speaker, an alarm or a screen embedded in or attachable to one of the arm rests, for example, so that the user can receive information or be alerted to a problem with their use of the chair. According to one embodiment of the invention, the screen could be an LCD screen 7 incorporated in one of the arm rests. Other types of screens could be used to notify the user of important information relating to the use of the chair, or other information which may be desired by the user.

The activity and presence sensor 10 can be located anywhere in the chair sufficient to determined whether the chair is occupied and the extent to which the person is moving to aid in determining whether the user is awake, asleep, etc.

The pressure sensors 12 are designed to detect the force with which the person sits down, or possibly, which of a plurality of preset users are occupying the chair at a particular time. The angle sensors 14 can detect how far the chair is raised and lowered, the angle of the foot rest (i.e., whether it is fully up, partially up, down, etc.).

Embedded within the chair may be a microcontroller 18 which controls the functioning of the chair and enables information about the usage of the chair and information from the various sensors to be calculated, stored and transmitted via a transmission device, either embedded in the chair (not shown) or separately connectable to the chair, to a third party via the Internet. The features enabled by the microcontroller 18 could include, but are not limited to, restricting how high a person can raise the chair or automatically raising the chair when it is determined the person should get up due to a pre-scheduled event or emergency. The transmission device may be a wireless communication device which connects the chair to the Internet, either directly or through a separate hub, allowing doctors, family, or external service providers to monitor the use of the chair and set parameters on how much help the chair will provide the user.

Figure 2:
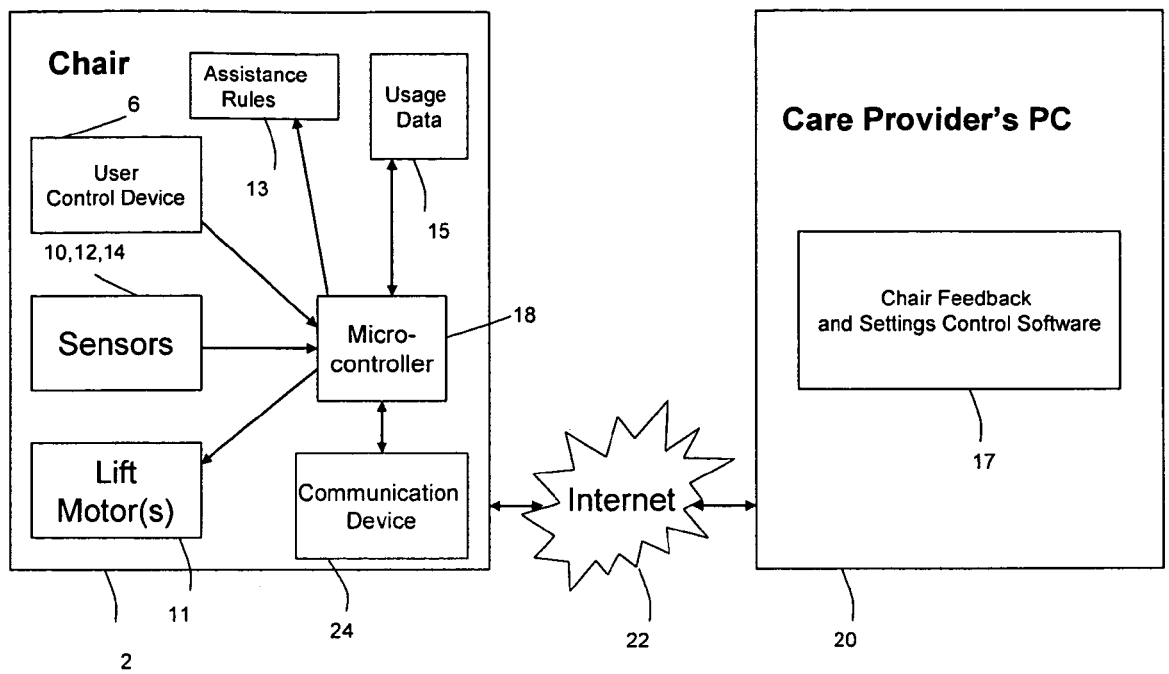
FIG. 2 shows an overall system according to an embodiment of the invention.

FIG. 2 illustrates the overall system according to an embodiment of the invention. As seen in FIG. 2, the information from the sensors 10, 12 and 14, information from the user control device 6 are input to the microcontroller 18. The microcontroller, in turn, can control the lift motor(s) 11 to operate the chair. At set-up, a starting set of parameters, or assistance rules, may be programmed in by a remote device 20, which can be a caregiver such as a doctor, to control how much assistance the chair will provide. The starting set of assistance rules can either be pre-loaded or sent to the microcontroller 18 from the care provider 20 via the Internet 22. The chair may be pre-loaded with a standard set of default parameters. The chair could operate in response to the user input through the user control device, but at the same time it could behave according to the assistance rules set by the care provider 20 or pre-set in the microcontroller 18 (the rules are stored in the chair's storage device). For example, when the user wants to stand up, the user could activate the lift control like a normal lift chair. However, the chair would stop lifting the user at the position defined by the rules. If the user needed additional assistance, they could use the override button to get the assistance they need. In cases of emergency, such as weakness, the user could still get the assistance they need, but in general, the user would get the exercise they need. Records of how many times they used the override feature could be stored and could be reviewed remotely by the care provider. In addition, general records of the chair's usage and information from the various sensors could be stored.

The sensors on the chair can record the user's interaction with the chair—how much force did they sit down with, how much they pushed off on the arm-rests to stand, how long are they staying seated for, how far are they reclining, etc. The chair could also be programmed to stimulate user movement, such as altering the angle of recline periodically, or forcing them to stand for a certain amount of time every few hours to encourage exercise and increase circulation. Any time the chair began an automated activity it could notify the user via the feedback device, and the user could stop the activity with the override button. The chair can be programmed so that it does begin automated activities if the user isn't in the chair as detected by the activity and presence sensor, and could be programmed not to start if the user is sleeping, as determined by the sensor. In addition, in a household where more than one user typically uses the chair, the pressure sensors could be used to determine, based on the respective weights of the users, which user is occupying the chair and apply rules designated for that particular user.

The chair preferably connects to the Internet 22 either through an communication device 24 on board the chair, such as a device to connect to an existing home network, to the Internet through a cell-phone network connection, or to the Internet through a wireless network. The communication device may be embedded in the chair or connected to the chair in a way commonly known in the art. The information from the microcontroller 18 may be sent to the care provider 20 via the communication device 24 over the Internet 22. The care provider 20 can connect via the Internet 22 to the chair in a variety of known ways. Information can be shared both ways between the chair and the care provider.

Periodically, the care giver could either remotely or locally review usage data and alter the assistance rules stored on the chair to take into account the changing condition of the patient.

Figure 3:
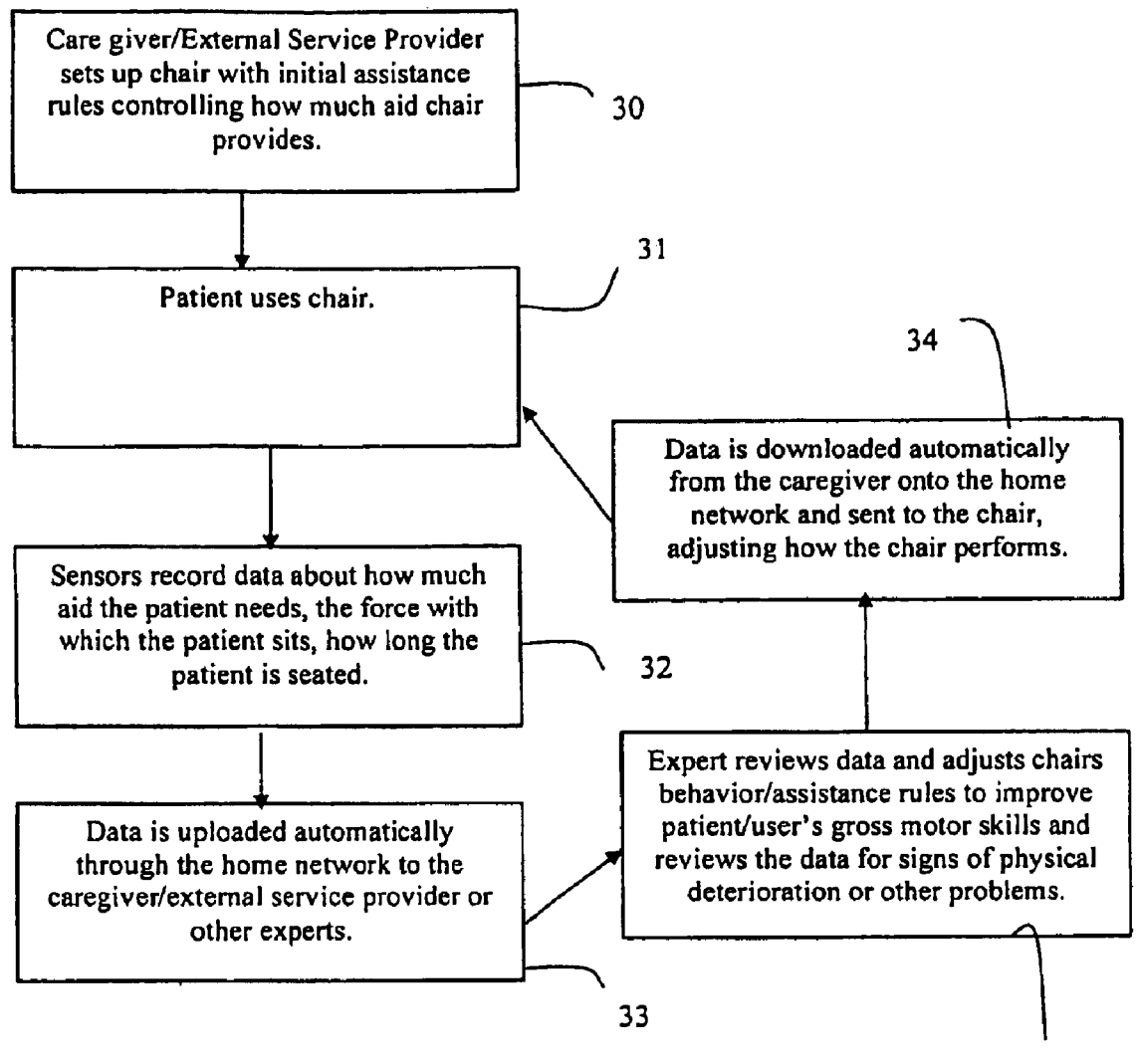
FIG. 3 is a flowchart which shows the chair according to an embodiment of the invention.

FIG. 3 is a flowchart which shows the operation of a system according to an embodiment of the invention. At 30, the care giver/external service provider sets up the chair with an initial set of assistance rules that controls how much aid the chair will provide. At 31, the patient/user uses the chair. At 32, the various sensors embedded in the chair record data about how much aid the patient needs, the force with which the patient sits, and how long the patient is seated. At 33, the data (usage data) is uploaded automatically through a home network, for example, to the caregiver. At 34, the data is downloaded automatically from the caregiver onto the home network and sent to the chair adjusting how the chair performs. At 35, the expert reviews the usage data and adjusts the chairs behavior/assistance rules to improve the patient's gross motor skills and reviews the usage data for signs of physical deterioration or other such problems.

Figure 4:
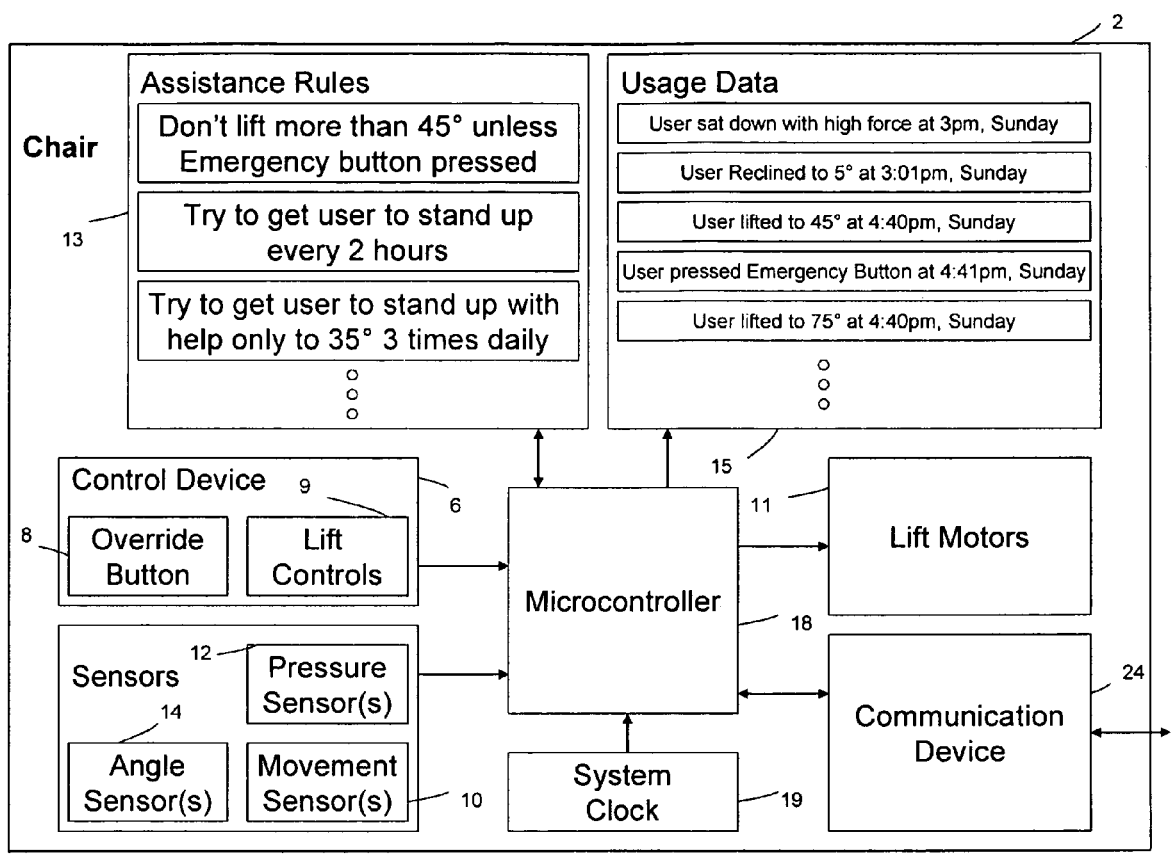
FIG. 4 shows an overall system according to an embodiment of the invention.

FIG. 4 is a diagram showing the chair according to an embodiment of the invention. As seen in FIG. 4, the chair 2 stores assistance rules 13 and usage data 2. An example of some assistance rules includes, "Don't lift more than 45° unless emergency button pressed," "Try to get user to stand up every 2 hours," and "Try to get user to stand up with help only to 35° 3 times daily." An example of the usage data stores is, "User sat down with high force at 3 pm, Sunday," "User Reclined to 5° at 3:01 pm, Sunday," "User lifted to 45° at 4:40 pm, Sunday," "User pressed Emergency Button at 4:41 pm, Sunday" and "User lifted to 75° at 4:40 pm, Sunday."

The control device 6 includes an override button 8 and lift controls 9, which control the operation of the chair. The sensors 10, 12 and 14 communicate information to the microcontroller 18. The information from the control device is also output to the microcontroller 18. A system clock 19 is also embodied in the chair to keep track of events, such as recorded in the usage data. The microcontroller 18 controls the lift motors 11 and transmits information over the communication device, preferably to a third party device, such as the caregiver/doctor.

All the lift chairs on the market do not have any means of collecting or providing feedback on how much aide the patient needs, nor do they have any method for controlling how much aid they provide the patient. The embodiments of this invention allows the patient's condition to be monitored and parameters to be set to ensure the patient gets the correct amount of aid.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A system comprising:
   a lift chair;
   a plurality of sensors embedded in the lift chair;
   a controller capable of controlling operation of the lift chair based on a set of assistance rules stored by the controller; and
   a communication device which is capable of communicating information from the plurality of sensors to a remote device,
   wherein the controller is adapted to determine which of a plurality of previously registered users is occupying the chair based on information detected from the sensors, and is adapted to control operation of the chair based on a pre-determined set of assistance rules stored for each respective user;

further wherein the plurality of sensors are configured to record said respective user's interaction with the lift chair and the controller is configured to control how much assistance the lift chair should provide to said respective user.

2. The system of claim 1, wherein the communication device is a two-way communication device.

3. The system of claim 1, further comprising a user control device capable of controlling operation of the lift chair.

4. The system of claim 1, wherein the remote device is capable of transmitting assistance rules to the controller via the communication device.

5. The system of claim 4, wherein the remote device is adapted to transmit the assistance rules via the Internet.

6. The system of claim 5, wherein the assistance rules are alterable by a remote caregiver via the remote device.

7. The system of claim 5, further comprising a notification device, the notification device being adapted to notify the user of changes in the assistance rules.

8. The system of claim 1, wherein the plurality of sensors includes at least one of activity and presence sensors, pressure sensors and angle sensors.

9. The system of claim 1, further comprising a user control device adapted to control operation of the chair, wherein the user control device includes an override button configured to override the stored assistance rules to control operation of the chair.

10. The system of claim 9, wherein the controller is adapted to store information from the user control device.

11. The system of claim 10, wherein the information stored from the user control device is capable of being transmitted to the remote device.

12. The system of claim 1, further comprising a notification device attached to the chair configured to receive information from the controller regarding operation of the chair and to relay the information to a user of the chair.

13. The system of claim 1, wherein the assistance rules are configured to control how high the chair can be raised.

14. The system of claim 1, wherein the plurality of sensors are capable of detecting information including at least one of a user's interaction with the chair, how much force the user sits down with, how much the user pushed off arm rests of the chair, how long the user remains seated in the chair, how far the chair is reclined, how far the chair is raised and lowered, and an angle of a foot rest of the chair.

15. The system of claim 14, wherein the information detected from the plurality of sensors is capable of being transmitted to the remote device via the Internet.

16. The system of claim 15, wherein the remote device is capable of transmitting a new set of assistance rules based on the information detected by the sensors.

17. A lift chair comprising:
a plurality of sensors embedded in the chair;
a controller capable of controlling operation of the chair; and
a storage device capable of storing information detected from the sensors,
wherein the controller is adapted to control operation of the lift chair based on a set of assistance rules stored by the controller and wherein the controller is adapted to control operation of the chair based on a pre-determined set of assistance rules stored for each respective user;
further wherein the plurality of sensor are configures to record said each respective user's interaction with the lift chair and the controller is configured to control how much assistance the lift chair should provide to said respective user.

18. The lift chair of claim 17, further comprising a user control device adapted to control operation of the lift chair.

19. The lift chair of claim 17, further comprising a user control device adapted to control operation of the lift chair based on a set of assistance rules stored by the controller, wherein the user control device includes an override button adapted to override the stored assistance rules to control operation of the chair.

20. The lift chair of claim 19, wherein the assistance rules control how high the chair can be raised.

21. The lift chair of claim 17, wherein the plurality of sensors includes at least one of activity and presence sensors, pressure sensors and angle sensors.

22. The lift chair of claim 17, further comprising a notification device attached to the chair adapted to receive information from the controller regarding operation of the chair and to relay the information to a user of the chair.

23. The lift chair of claim 17, wherein the assistance rules control how high the chair can be raised.

24. The lift chair of claim 17, wherein the plurality of sensors are capable of detecting information including at least one of a user's interaction with the chair, how much force the user sits down with, how much the user pushed off arm rests of the chair, how long the user remains seated in the chair, how far the chair is reclined, how far the chair is raised and lowered, and an angle of a foot rest of the chair.

25. The lift chair of claim 17, further comprising a user control device adapted to control operation of the chair, wherein the user control device includes an override button configured to override the stored assistance rules to control operation of the chair.

26. A system comprising:
a lift chair;
a plurality of sensors embedded in the lift chair;
a storage device capable of storing information detected by the plurality of sensors;
a controller adapted to control operation of the lift chair in accordance with a set of assistance rules, wherein the controller is adapted to control operation of the chair based on a pre-determined set of assistance rules stored for each respective user; and
a communication device adapted to communicate information from the plurality of sensors to a remote device;
further wherein the plurality of the sensors are configured to record said each respective user's interaction with the lift chair and the controller is configured to control how much assistance 27. The system of claim 26, wherein the remote device is adapted to transmit assistance rules to govern operation of the chair to the communication device of the chair.

28. The system of claim 27, wherein the remote device is adapted to transmit the assistance rules via the Internet.

29. The system of claim 26, wherein the plurality of sensors include sensors which are adapted to determine an amount pressure exerted on respective portions of the chair.

30. The system of claim 26, wherein the plurality of sensors include sensors which are adapted to determine an activity level of a user of the chair.

31. The system of claim 26, further comprising a user control device with an override button, wherein the assistance rules can be overridden and control of the chair is adapted to be performed only through use of the user control device.

* * * * *

UNITED STATES PATENT AND TRADEMARK OFFICE
CERTIFICATE OF CORRECTION

PATENT NO. : 7,461,896 B2  Page 1 of 1
APPLICATION NO. : 11/478526
DATED : December 9, 2008
INVENTOR(S) : Devon M. Welles et al.

It is certified that error appears in the above-identified patent and that said Letters Patent is hereby corrected as shown below:

In column 5, line 2, after "said" insert -- each --.

In column 5, line 5, before "respective" insert -- each --.

In column 5, line 63, delete "sensor" and insert -- sensors --, therefor.

In column 5, line 63, delete "configures" and insert -- configured --, therefor.

In column 5, line 67, before "respective" insert -- each --.

In column 6, line 46, before "sensors" delete "the".

In column 6, line 49, after "assistance" insert -- the lift chair should provide to said each respective user. --.

Signed and Sealed this

Twenty-fourth Day of February, 2009

JOHN DOLL
*Acting Director of the United States Patent and Trademark Office*